United States Patent
Parsee et al.

(10) Patent No.: US 8,852,148 B2
(45) Date of Patent: Oct. 7, 2014

(54) INFUSION PUMP HAVING FUNCTION KEYS

(75) Inventors: Mehryar Michael Parsee, Los Angeles, CA (US); Charles Grey, Irvine, CA (US); Sab Mirza, Laguna Niguel, CA (US)

(73) Assignee: Curlin Medical Inc., East Aurora, NY (US)

( * ) Notice: Subject to any disclaimer, the term of this patent is extended or adjusted under 35 U.S.C. 154(b) by 922 days.

(21) Appl. No.: 11/264,420

(22) Filed: Nov. 1, 2005

(65) Prior Publication Data

US 2007/0098565 A1    May 3, 2007

(51) Int. Cl.
- A61M 37/00    (2006.01)
- A61M 5/142    (2006.01)
- F04B 43/00    (2006.01)
- F04B 43/08    (2006.01)
- A61M 5/14    (2006.01)

(52) U.S. Cl.
CPC ........ *A61M 5/14228* (2013.01); *F04B 43/0081* (2013.01); *F04B 43/082* (2013.01); *A61M 2205/14* (2013.01); *A61M 2005/1405* (2013.01)
USPC .......................................... 604/131; 604/151

(58) Field of Classification Search
USPC ......... 604/31, 67, 65, 66, 131, 151, 152, 153, 604/81, 246, 500, 890.1, 891.1; 417/1, 12, 417/326, 44.1; 73/40, 149
See application file for complete search history.

(56) References Cited

U.S. PATENT DOCUMENTS

| | | | |
|---|---|---|---|
| 2,877,714 A | 3/1959 | Sorg | |
| 5,575,631 A * | 11/1996 | Jester | 417/474 |
| 5,630,710 A * | 5/1997 | Tune et al. | 417/326 |
| 5,681,285 A * | 10/1997 | Ford et al. | 604/151 |
| 5,683,233 A | 11/1997 | Moubayed et al. | |
| 5,685,844 A * | 11/1997 | Marttila | 604/65 |
| 5,713,856 A * | 2/1998 | Eggers et al. | 604/65 |
| 5,719,761 A * | 2/1998 | Gatti et al. | 700/1 |
| 5,764,034 A | 6/1998 | Bowman et al. | |
| 5,791,881 A | 8/1998 | Moubayed et al. | |
| 5,814,015 A * | 9/1998 | Gargano et al. | 604/67 |
| D408,911 S | 4/1999 | Moubayed et al. | |
| 5,924,852 A | 7/1999 | Moubayed et al. | |
| 5,935,099 A * | 8/1999 | Peterson et al. | 604/65 |
| 6,164,921 A | 12/2000 | Moubayed et al. | |
| 6,231,560 B1 * | 5/2001 | Bui et al. | 604/500 |
| 6,241,704 B1 * | 6/2001 | Peterson et al. | 604/65 |

(Continued)

FOREIGN PATENT DOCUMENTS

EP    0319272 A2    6/1989

OTHER PUBLICATIONS

Supplementary European Search Report for EP06826621 dated Oct. 7, 2010; Curlin Medical Inc.; 5 pages.

*Primary Examiner* — Kevin C Sirmons
*Assistant Examiner* — Phillip Gray
(74) *Attorney, Agent, or Firm* — Hodgson Russ LLP (57) ABSTRACT

An infusion pump having a plurality of function keys which initiate different processes depending on the state of the infusion pump is disclosed. In the configuration state, the function keys operate to set the various configurable options with regard to the desired medication treatment parameters. In the infusing state, the function keys operate to transmit various operational data to a readout screen depending on the function key pressed. Essentially, multi-function, state dependent function keys operable on an infusion pump is disclosed.

17 Claims, 7 Drawing Sheets

(56) References Cited

U.S. PATENT DOCUMENTS 6,371,732 B1 4/2002 Moubayed et al.
6,648,821 B2 * 11/2003 Lebel et al. .................. 600/300
6,768,425 B2 * 7/2004 Flaherty et al. .......... 340/870.07
2003/0163223 A1 8/2003 Blomquist
2004/0019607 A1 * 1/2004 Moubayed et al. ........ 707/104.1
2004/0064435 A1 4/2004 Moubayed et al.
2005/0143864 A1 * 6/2005 Blomquist .................... 700/282

* cited by examiner

```
┌─────────────────────────┐       ┌─────────────────────────┐
│    DATE AND TIME        │       │   POWER SOURCE          │
│    23JAN03  17:16       │       │   INTERNAL POWER        │
│                         │       │ [▨▨▨▨..................] │
│                         │       │  E   1/4   1/2   3/4  F │
└─────────────────────────┘       └─────────────────────────┘
         FIG. 8A                          FIG. 8B
```

```
┌─────────────────────────┐       ┌─────────────────────────┐
│▨│OPTIONS Lock OFF       │       │▨│HR  VOL-ml   BG  BA    │
│P│DN Occlu: HIGH         │       │P│19  -- --   -- --     │
│C│AIRSENS: 0.5    ml     │       │C│20  -- --   -- --     │
│A│AUDIO: 9               │       │A│▨21▨▨▨4.8▨▨0▨▨0▨      │
└─────────────────────────┘       └─────────────────────────┘
```

```
┌─────────────────────────┐       ┌─────────────────────────┐
│▨│   UNITS:  [mg]        │       │▨│BASL RATE: 0.0  ml/hr  │
│P│ CONCEN: 0.0   mg/ml   │       │P│    BOLUS: 0.0  ml     │
│C│ ADMIN Rt: IV          │       │C│ BOLS INT: 0    MIN    │
│A│ LOAD DOSE: 0.0   mg   │       │A│ #BOLS/HR: 0           │
└─────────────────────────┘       └─────────────────────────┘
```

```
┌─────────────────────────┐       ┌─────────────────────────┐
│▨│   PERCENT BOLUS       │       │▨│Cleared: 24JAN 21:35   │
│P│ TBOL:  5.0  ml        │       │P│  Vol INF: 3.5   ml    │
│C│ TVOL: 10.0  ml        │       │C│ Pt. BOLUS: 0 of 0     │
│A│  % BOLS: 50           │       │A│   DONE?               │
└─────────────────────────┘       └─────────────────────────┘
```

INFUSION PUMP HAVING FUNCTION KEYS

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

This invention generally relates to infusion pumps. More particularly, this invention relates to infusion pumps having function keys for recalling critical operational data during medication infusion.

2. Description of the Related Art

Means for supplying patients with fluid medication for sustained periods in a controlled manner is well known in the art. One such commonly known and well recognized means is a bag filled with fluid medication which was fed into the patient by gravitational force through intravenous tubing having drip or other controllers. More specifically, a sterile container such as a glass or plastic bottle, or a plastic bag was attached to one end of a drip chamber, and the other end of the same was attached to a tube. The drip chamber allowed the fluid to flow one drop at a time, and the tube had an attached hollow needle that was inserted into the vein. Further connectors could be attached to the tube, which permitted other fluid medication to be delivered through the same needle. The adjustability of the flow rate in such prior devices was quite limited, however, and a variety of expensive and complicated flow control valves and devices have been developed. Where fluctuations in the flow rate were not critical, the aforementioned gravity drip system continues to be used for its utter simplicity.

In an attempt to obtain even greater control over the flow rate, peristaltic and other electrically driven pumps were developed. Conventional peristaltic pumps typically have a section of resilient tubing positioned between a wall and a set of rollers or reciprocating pushers that progressively compress sections of tubing to facilitate the pumping of a liquid therethrough. Such peristaltic pumps known in the art include teachings from U.S. Pat. No. 2,877,714 to Sorg, et al. Improvements thereto have also been made, such as those teachings of a curvilinear peristaltic pump in U.S. Pat. No. 6,371,732 to Moubayed, et al., a linear peristaltic pump in U.S. Pat. No. 5,924,852 to Moubayed, et al., and a curvilinear peristaltic pump with occlusion detection means in U.S. Pat. No. 5,791,881 to Moubayed, et al., which are wholly incorporated by reference herein.

In the more advanced infusion pumps, all aspects of operation came to be governed by a central processing unit. A software application running on a microcontroller within the pump selectively transmitted signals to a motor that drove the pump based on the parameters interactively set by the user via input from a keypad while viewing the results of that interaction on readout displays. Memory modules operatively connected to the microcontroller stored the operator inputted parameters, as well as the various interactive menus which were presented to guide the operator through the various settings. In general, the microcontroller was understood to be in two separate states—the first being the configuration stage, where the operator could navigate a series of on-screen menus to select the appropriate treatment for a patient, and the second being the infusing stage, where the previously set treatment was administered to the patient. While the function keys enabled the operator to interact with the pump during the configuration stage, the keys provided no functionality while in the treatment phase, and merely provided a miniscule amount of information related to the current state of the treatment. Since the screen size was limited, there was no way to provide all of the relevant information at once.

Therefore, there is a need in the art for an infusion pump having the ability to selectively display operational information. Further, there is a need for an infusion pump having function keys which enabled the operator to configure the operational parameters during a configuration stage, and the same function keys enabling the operator to view relevant data while the treatment is being administered. Still further, there is a need in the art for an infusion pump with function keys which retrieves and groups a series of relevant data and displays the same on a screen by activating a particular key, and which retrieves and groups another series of relevant data and displays the same on a screen by activating another particular key. These needs and more are fulfilled by the present invention, the details of which are discussed more fully below.

BRIEF SUMMARY

In light of the foregoing limitations, the present invention was conceived. According to one aspect of the present invention, provided is an infusion pump having a first state and a second state, for infusing fluid medication, comprising a data processor, a readout screen electrically connected to the data processor, and a plurality of function keys electrically connected to the data processor. Further, at least one of the function keys is operable to activate a first data processing operation on the data processor while the infusion pump is in the first state, and is operable to activate a second data processing operation on the data processor while the infusion pump is in the second state. There is further a memory module electrically connected to the data processor, in which the memory module stores results from the first and second data processing operations. The infusion pump may further comprise a platen, a rotatable cam assembly spaced from the platen, a set of spaced pump finger assemblies, each having a first end riding on the cam and a second end adjacent to the platen, and a resilient tube interposed between the platen and the pump finger assemblies.

According to another aspect of the present invention, there is a data input port electrically connected to the data processor and a bolus, for transmitting a bolus activation signal from the bolus to the data processor.

According to yet another aspect of the present invention, the aforementioned first state is while the infusion pump is infusing the fluid medication, and the aforementioned second state is while the infusion pump is not infusing the fluid medication. The first data processing operation is the displaying of operational data on the readout screen, and can also be the holding of an output to the readout screen for a set time period. Additionally, it may be the clearing of data from the memory module.

In accordance with still another aspect of the present invention, the second data operation is setting the operational configuration of the infusion pump and transmitting data to the readout screen. In one aspect of the present embodiment, the operational data comprises the date and time, while in another aspect the operational data comprises electrical power source information. Still further, the operational data may comprise currently set global options, and may also comprise a log of infusion history. The operational data may also comprise currently set fluid medication infusion options. Finally, the operational data may comprise a log of bolus activation history.

According to another aspect of the present invention, an infusion pump comprises a plurality of function keys, at least one of the function keys upon activation transmits a signal to a central processor unit having an infusing state and a non-infusing state. The signal activates a data transmission to a display while the central processor unit is an infusing state, and modifies one or more configuration settings recorded in the central processor unit and initiates a data transmission to the display when the central processor unit is in a non-infusing state.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The detailed description set forth below in connection with the appended drawings is intended as a description of the presently preferred embodiment of the invention, and is not intended to represent the only form in which the present invention may be constructed or utilized. The description sets forth the functions and the sequence of steps for developing and operating the invention in connection with the illustrated embodiment. It is to be understood, however, that the same or equivalent functions and sequences may be accomplished by different embodiments that are also intended to be encompassed within the spirit and scope of the invention. It is further understood that the use of relational terms such as first and second, top and bottom, and the like are used solely to distinguish one from another entity without necessarily requiring or implying any actual such relationship or order between such entities.

With reference to FIGS. 1a, 1b, 1c and 1d, a well known infusion pump 10 is adapted to facilitate the pumping of a liquid through tubing assembly 12 from input side 13 to output side 14. Housing 16 includes a front housing half 18a and a back housing half 18b which are rigidly attached to each other through the use of fasteners such as screws, though alternative attachment methods may also be employed in relation thereto. The front housing half 18a is provided with function keypad 20, and a display 22. The back housing half 18b is provided with a removable door 24 for accessing a battery storage compartment within the interior of housing 16. The front and back housing halves 18a, 18b are preferably fabricated from a plastic material, though alternative lightweight materials may be used for the fabrication thereof. In addition to the front and back housing halves 18a and 18b, housing 16 comprises a support member 25 which defines a channel having a generally U-shaped cross-sectional configuration. Support member 25 is attached to the front and back housing halves 18a and 18b such that the channel defined thereby extends longitudinally between the upper ends of the front and back housing halves 18a and 18b.

Figure 1A:
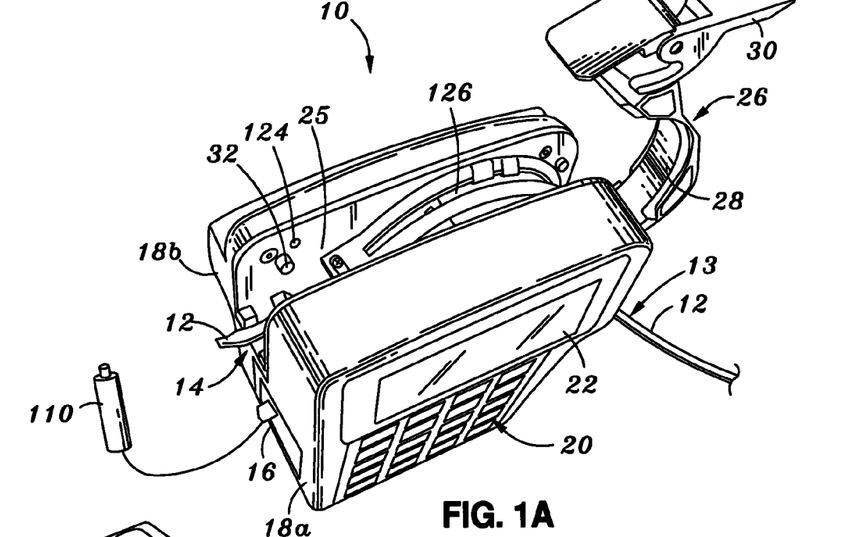
FIG. 1a a top frontal perspective view of a infusion pump with the platen in a non-operative position and a bolus electrically and fluidly connected thereto in accordance with one aspect of the present invention.
Figure 1B:
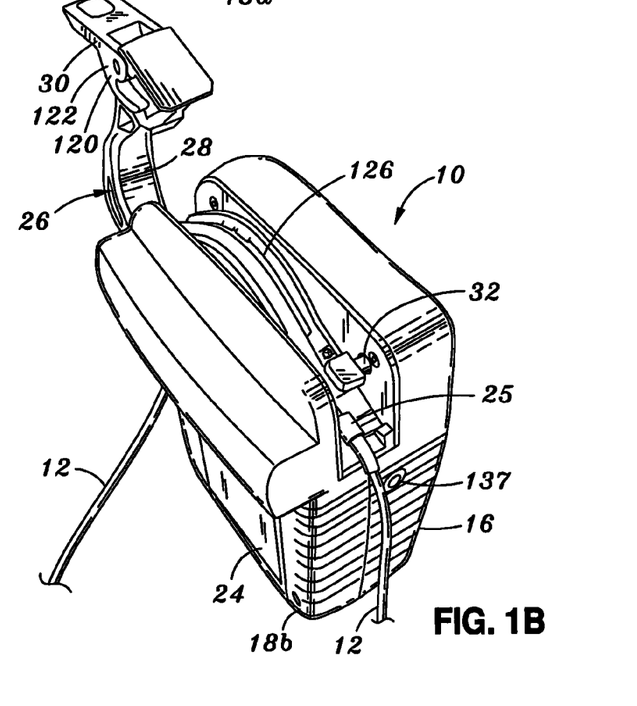
FIG. 1b is top posterior perspective view of an infusion pump with the platen in a non-operative position in accordance with one aspect of the present invention.
Figure 1C:
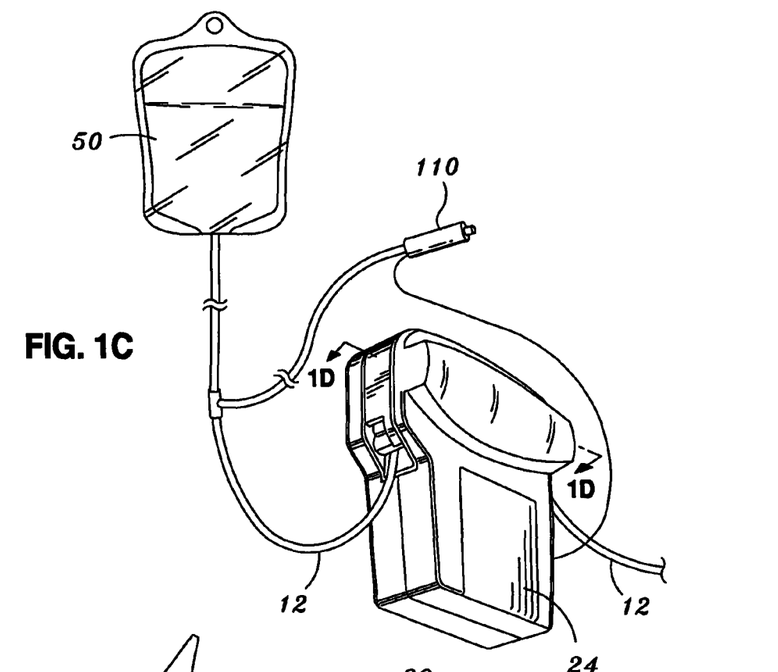
FIG. 1c is a bottom posterior perspective view of infusion pump the tube assembly passing therethrough with an attached fluid medication supply and a bolus in accordance with one aspect of the present invention.

The pump 10 further comprises a platen member 26 which is pivotally connected to support member 25 of housing 16 and moveable between an operative position (as shown in FIG. 1c) and a non-operative position (as shown in FIGS. 1a, 1b). Platen member 26 defines an arcuate, generally concave inner surface 28. When platen member 26 is in its operative position, it resides within the channel defined by support member 25, with the inner surface 28 being shielded thereby. The platen member 26 is provided with an over-the-center latch mechanism 30 on the end thereof opposite that pivotally connected to support member 25. Latch mechanism 30 is cooperatively engageable to a pair of latch pins 32 protruding from respective ones of opposed inner surfaces of support member 25 into the channel defined therebetween. As will be readily understood, the engagement of latch mechanism 30 to latch pins 32 maintains or locks the platen member 26 within its operative position.

Figure 1D:
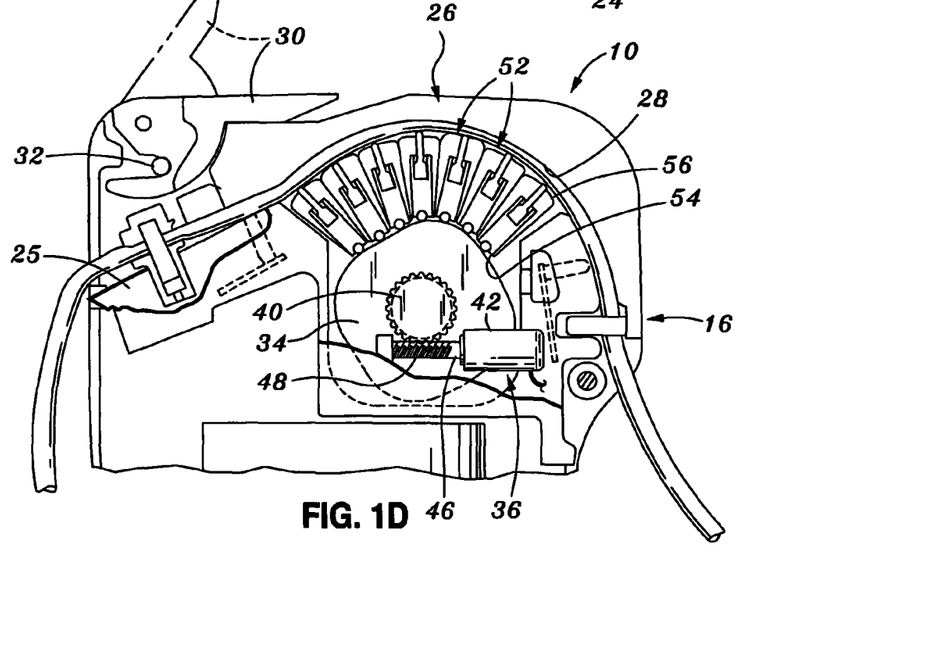
FIG. 1d is a front cross-sectional view of the internals of an infusion pump in accordance with an aspect of the present invention.

Referring to FIG. 1d, Pump 10 additionally includes a platen sensor 120 which is operable to detect when platen member 26 is in its operative position. Preferably, platen sensor 120 is a Hall effect sensor which comprises a magnet 122 disposed within over-the-center latch mechanism 30 of platen member 26. In addition to magnet 122, platen sensor 120 includes magnetic field detector 124 which is disposed within support member 25 in close proximity to one of the latch pins 32 protruding therefrom. Magnetic field detector 124 is oriented so as to be disposed directly adjacent to magnet 122 when platen member 26 is moved to its operative position and latch mechanism 30 engaged to latch pins 32.

Further, pump 10 comprises a rotating cam 34 which is disposed within the interior of housing 16 and rotatably mounted to support member 25. More particularly, cam 34 is mounted to support member 25 so as to be rotatable about an axis which extends through the approximate center of the concavity of arcuate inner surface 28 of platen member 26 when platen member 26 is in its operative position. Rotation of cam 34 is facilitated by a drive unit 36 of pump 10 which is also disposed within the interior of housing 16 and attached to support member 25. Drive unit 36 is mechanically coupled to cam 34 such that the activation of drive unit 36 results in the concurrent rotation of the same in a first direction, and the deactivation of drive unit 36 maintains cam 34 in a set position. By way of example only and not of limitation, drive unit 36 comprises a cam shaft 46 and a worm 48 attached thereto, and a variable speed electric motor 42, and worm gear 40 cooperating with worm 48, the engagement of which transfers rotational motion from the electric motor 42 to cam 34.

Additionally, pump 10 further comprises a plurality of pump fingers 52 which are movably attached to the support member 25 and are arranged in side-by-side relation to each other so as to define an arcuate row. Each of the pump fingers 52 has a first end 54 which is cooperatively engaged to cam 34 and a second end 56 which is disposed in spaced relation to platen member 26 when the same is in its operative position. Pump 10 also includes pliable membrane 126 which is preferably fabricated from a transparent or translucent material and is attached to support member 25 so as to cover second ends 56 of pump fingers 52. Moreover, membrane 126 is preferably formed to have a thickness of about 0.0007 inches, and is exposed when platen member 26 is in its non-operative position. In this regard, as cam 34 is rotated, pump fingers 52 correspondingly rise and fall with the motion, sequentially squeezing tube assembly 12 along arcuate inner surface 28 of platen member 26. Thus, by suction force, fluid medication flowing into tube assembly 12 is conveyed from input end 13 to output end 14. As understood, input end 13 is connected to a fluid medication container 50, and can be a plastic bag, a syringe, or any other suitable container. While the particulars of a curvilinear peristaltic infusion pump have been heretofore described, a person having ordinary skill in the art will readily recognize that the present invention is not limited to such an infusion pump, and, in fact, any infusion pump operating under any one of many principles and any configuration will be understood to be encompassed within the scope of the present invention. Of course, such person will also recognize that any infusion pump so encompassed will be electronically controlled by a central data processor.

With reference to FIG. 1c, it may also be desirable to include an electronically controlled bolus 110 containing a separate medication for on-demand infusion into a patient. It will be understood that a bolus typically dispenses pain reducing medication upon activation, typically via a pushbutton, by a patient. Bolus 110 is in fluid communication with tube assembly 12, and is also in electrical communication with pump 10 through data input port 16 for recording the activations.

Figure 2:
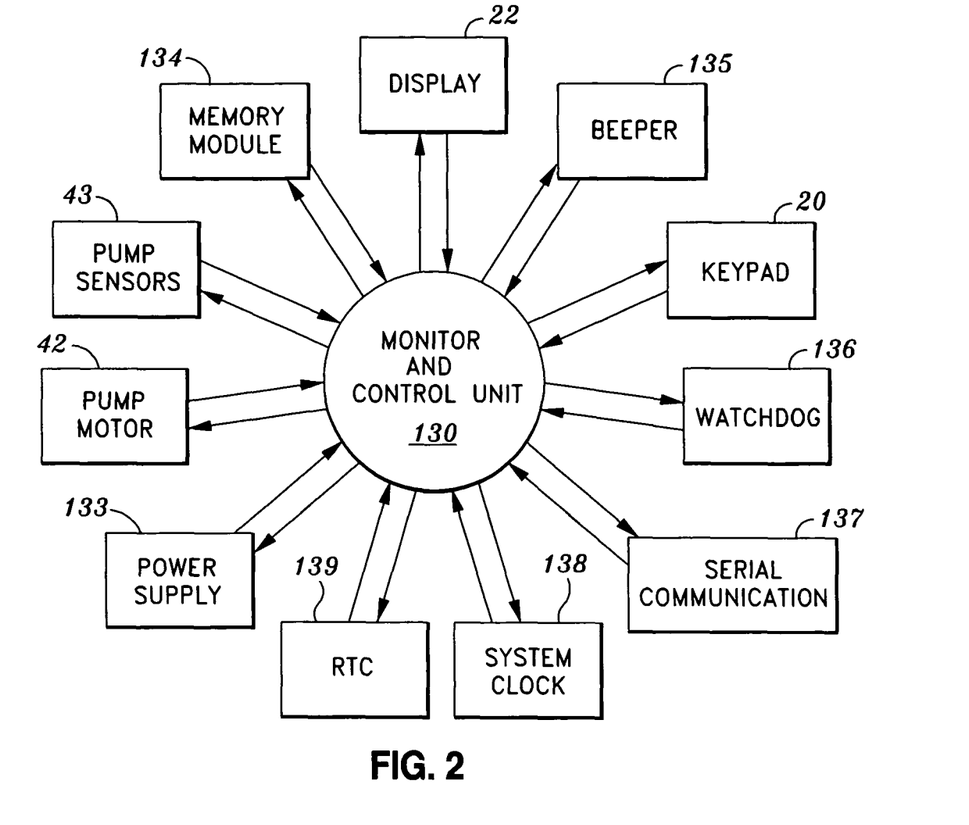
FIG. 2 is a block diagram showing the interrelated peripherals of an infusion pump in accordance with an aspect of the present invention.

With reference to FIGS. 1a and 2, pump 10 of the present invention is provided with an internal monitor and control unit 130 comprised of a programmable data processing device which monitors, controls, and coordinates the various operations thereof. The monitor and control unit 130 implements software of a specific design an architecture which imparts various functional attributes which will be described in further detail hereunder.

The monitor and control unit 130 is in electrical communication with a variety of components of pump 10. Power supply 133 supplies electrical power to monitor and control unit 130 and all of the peripherals requiring power which are connected thereto, including, but not limited to, pump motor 42, pump sensors 43, memory module 134, display 22, beeper 135, keypad 20, watchdog 136, serial communications 137, system clock 138, and real-time clock 139. Preferably, power supply 133 is comprised of one or more batteries enclosed within housing 16, and may include additional circuitry for increasing the voltage or current. Additionally, power supply 133 may comprise of a connection to an external DC source which draws power from a conventional 120V, 60 Hz Alternating Current household power outlet, with accompanying rectifying and voltage regulating circuitry well known in the art. As will be apparent, any one of numerous power supplies may be utilized, although it is preferable to use a battery due to its reliability and independence from the oft unreliable power grid.

Also in electrical communication with monitor and control unit 130 is a beeper 135 of pump 10 which is disposed within the interior of housing 16. Beeper 135 contains two buzzers which operate at a single, fixed frequency. One of the buzzers, which is designated as the normal operation buzzer, is pulsed at varying widths, pulse rates and total number of pulses, as a function of the event to be signaled thereby. The second buzzer, which is designated as an auxiliary buzzer, operates from a watch dog time out. The second buzzer can be tested once and then reset via a clear auxiliary beeper input event. Additionally, monitor and control unit 130 is in electrical communication with system clock 138, which is a processor timer interrupt which is set at approximately 53.3 milliseconds.

Furthermore, also in electrical communication with monitor and control unit 130 is a real time clock 139, a watch dog 136, and a serial communications port 137. Real time clock 139 provides a reference for the date and time of day, with this information being read therefrom on demand. The serial communications port 137 is preferably an asynchronous serial port, 9600 bps full duplex, with no RTS or CTS, RDX and TXD only. Typically, serial communications port 137 is connected to bolus 110 to provide monitor and control unit 130 with a signal when a user activates bolus 110. The watch dog 136 is an independent, re-triggered one shot which is attached to a microcontroller NMI input and a motor inhibit control input of pump 10. It must be "petted" at least once every 1.6 seconds to prevent triggering the aforementioned auxiliary beeper, and also provides a test capability which can be activated to cause watch dog 136 to time out but not reset the microcontroller of pump 10 one time after the power-up thereof.

In addition to the foregoing, monitor and control unit 130 is electrically connected to pump motor 42 and pump sensors 43. As described above, pump motor 42 facilitates the rotation of cam 34, and hence drives pump 10. Based on the conditions as set forth programmatically in monitor and control unit 130, signals are transmitted to pump motor 42. It is understood that while monitor and control unit 130 can generate the pulse width modulated signals required to drive pump motor 42, the power of such signal is substantially lower than necessary. Furthermore, it is desirable to electrically isolate the motor components from monitor and control unit 130. Accordingly, the signal is transmitted to an intermediate motor driver circuit prior to reaching pump motor 42. In order to monitor the safe operation of pump 10, a variety of pump sensors 43 transmit signals to monitor and control unit 130, among which include platen sensor 120, tubing pressure sensors, air-in-line sensors, and so forth.

In order to provide configurability and the ability to interactively operate pump 10, monitor and control unit 130 is electrically connected to keypad 20, display 22, and memory module 134. Key pad 20 has a nineteen (19) key configuration, each of which is operative to transmit a signal to monitor and control unit 130 and alter the operational sequence thereof. Additionally, display 22 preferably consists of a 100× 32 dot matrix Liquid Crystal Display (LCD), and is used to provide an output means for the user to interact with pump 10. It will be understood that monitor and control unit 130 transmits to display 22 a series of bits representative of characters and the formatting thereof. This data is received by a LCD driver which converts such characters and interprets those formatting instructions, and accordingly activates and deactivates the appropriate pixels on the LCD screen. Still further, memory module 134 stores any data transmitted from monitor and control unit 130 when signaled to do so thereby, as well as transmit data to control unit 130 when signaled to do so thereby. It will be appreciated that any one of numerous memory types including, but not limited to, Read Only Memory (ROM) Dynamic Random Access Memory (DRAM), Static Random Access Memory (SRAM), and Non-Volatile Random Access Memory (NVRAM) such as Electrically Erasable and Programmable Read Only Memory (EEPROM), a subset of which includes Flash memory, or any combination thereof, may be utilized. For example, the program which controls the operation of pump 10 may be stored in ROM, while configuration settings and operational parameters may be stored on Flash memory.

Figure 3:
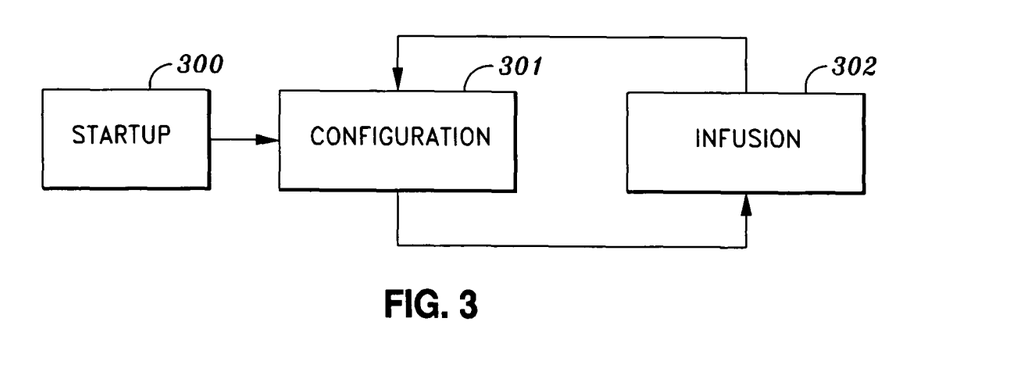
FIG. 3 is a block diagram showing the various states of an infusion pump in accordance with an aspect of the present invention.

Still referring to FIG. 2, and now, additionally to FIG. 3, monitor and control unit 130 is said to have generally two operating states: the configuration state 301 and the infusion state 302. Within this framework, and with reference now to FIGS. 4 and 5, further details of the configuration state will now be discussed. Upon powering on pump 10 via an input from keypad 20, specifically on/off key 501 in power-on step 401, monitor and control unit 130 begins an initialization sequence, which, among other things, transmits "splash" screens to display 22 containing manufacturer/developer information, and calibrates pump motor 42 and pump sensors 43. This step may also additionally involve retrieving such information from memory module 134.

Figures 4, 4A:
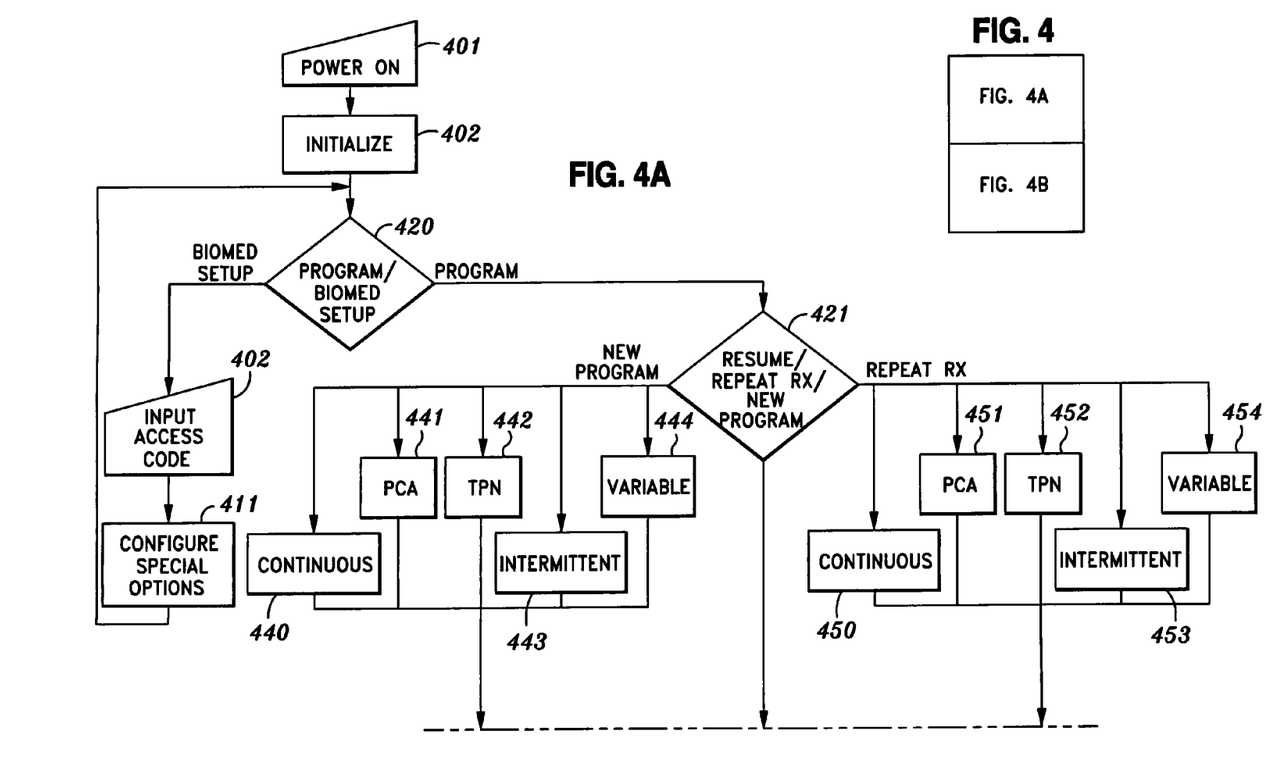
FIG. 4 is a flowchart for aiding in describing the configuration state of an infusion pump in accordance with an aspect of the present invention.
Figure 4B:
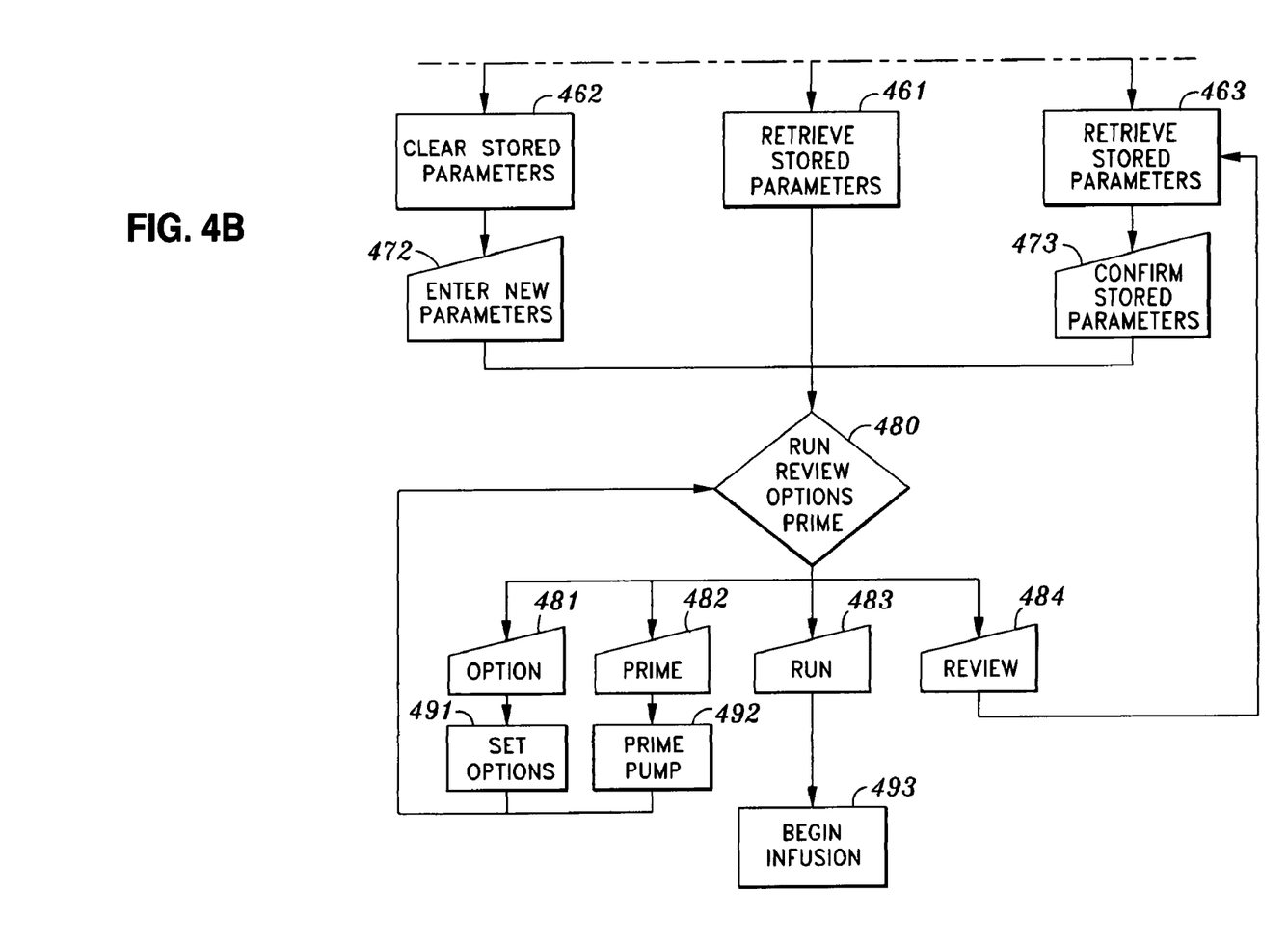
Figure 5:
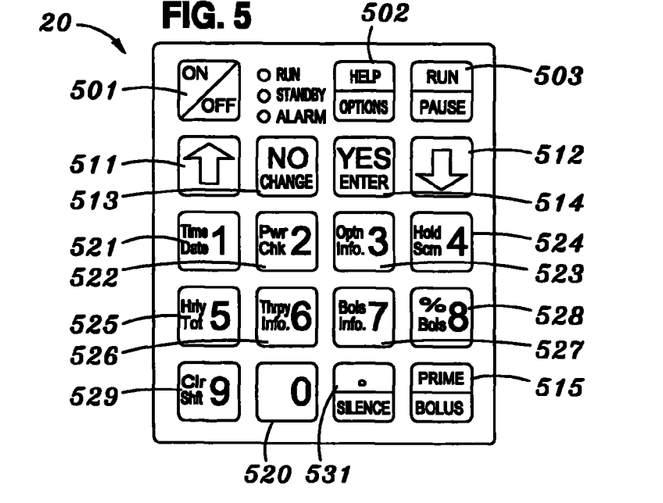
FIG. 5 is a front view of a keypad in accordance with one aspect of the present invention.

Following initialization, the operator is presented to make a selection 420 between either PROGRAM or BIOMED SETUP. In order to select between the options, the user presses up key 511 or down key 512 to move the text highlight on display 22, and when a desired function is highlighted, the user presses the YES/enter key 514 to initiate or choose that function. If BIOMED SETUP is chosen, the user is then presented to enter an access code as in step 402. The access code is a numerical value, and can be entered through numerical keys 520-529. If access is granted, the user may perform special setup functions 411 including printing history files and other pertinent data of a patient, as well as "factory calibration" which provides for the calibration of the pump 10. Alternatively, if PROGRAM is selected, the user is then presented with a selection 421 which include RESUME, for resuming an existing therapy previously recorded yet incomplete, REPEAT RX, for repeating an existing therapy which had been completed, and NEW PROGRAM, for clearing an existing therapy and entering a new one.

Where either NEW PROGRAM or REPEAT RX is selected, the user is presented with a menu to select the various treatments available, including CONTINUOUS 440 or 450 (depending on whether NEW PROGRAM or REPEAT RX was selected), PCA 441 or 451, TPN 442 or 452, INTERMITTENT 443 or 453, and VARIABLE 444 or 453. As understood, the aforementioned abbreviations and words for treatments have further meanings as follows:

1. CONTINUOUS—Continuous infusion, designed to allow a constant programmed rate of infusion;
2. PCA—Patient Controlled Analgesia, designed for therapies that require a continuous rate of infusion, patient controlled demand boluses, or both;
3. TPN—designed to allow a level rate of infusion of parenteral nutritional products with the option of tapering at the beginning, end, or both of the infusion, and having an early ram-down feature;
4. INTERMITTENT—Intermittent delivery, designed to deliver programmed intervals and rates of specified amounts of the infusion between doses to keep the patient's access site patent; and
5. VARIABLE—Variable program, designed to allow varying amounts rates and times of delivery of infusions up to twenty four specified programs.

If NEW PROGRAM is initially selected, the stored parameters for the respective treatments are cleared in step 462, and queried to enter new parameters in step 472. Where REPEAT RX is initially selected, previously recorded parameters are retrieved from memory module 134 as in step 463, and the user confirms those retrieved parameters as set forth in step 473.

Figure 6A:
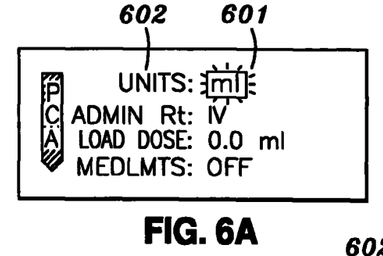
FIGS. 6a-6c are exemplary displays of configuration screens when modifying a parameter selectable from a finite list in accordance with one aspect of the present invention.
Figure 6B:
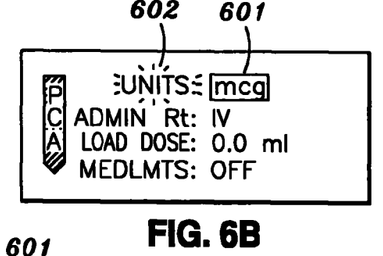
Figure 6C:
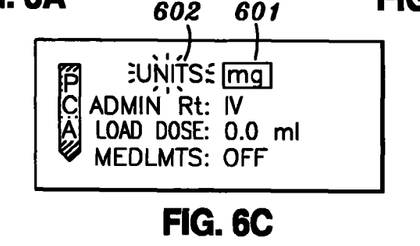

Although the set of parameters queried for will vary according to the treatment selected, the input method is identical across all treatments. For example, as shown in FIG. 6a, the setting selected for modification is the unit of measure, and is indicated as such by the flashing and highlighted parameter 601 displayed as ml. In order to modify this setting, the NO/Change key 513 is pressed, and cycles to the next available parameter 601. Thereafter, as shown in FIG. 6b, this is shown as "mcg." Now, descriptor 602 flashes to indicate that the unit of measure is being modified. Depressing the NO/Change key 513 again will cycle parameter 601 to display "mg" as shown in FIG. 6c, with descriptor 602 still flashing. Once parameter 601 is cycled to a desired setting, the operator can press any one of the YES/Enter key 514, up arrow key 511, or down arrow key 512, which is operable to record the setting into memory module 134 and cycles the flashing and highlighted parameter 601 to the next or previous line, depending on the key pressed. Accordingly, parameters having a finite list of available settings, including simple YES or NO parameters, can be altered in this manner.

Figure 7A:
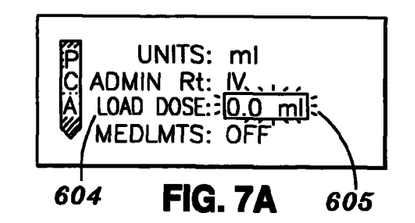
FIGS. 7a-7b are exemplary displays of configuration screens when modifying a numerical parameter in accordance with one aspect of the present invention.
Figure 7B:
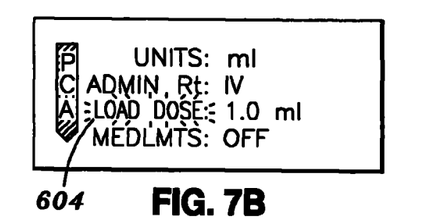

Referring now to FIGS. 7a-7c, now specifically FIG. 7a, the input method for setting numerical values will be described. Using up and down arrow keys 511 and 512 are pressed to cycle through to select numeric parameter 605. Upon selection, such is indicated by the highlighting and flashing of numeric parameter 605. Thereafter, values may be entered through keypad 20, specifically numerical keys 520-529. As illustrated in FIG. 7b, once a value has been entered, descriptor 604 begins flashing. In order to commit the value to memory module 134, YES/Enter key 514 must be pressed, and the flashing highlight will move to the next line. If either one of up or down arrow keys 511 or 512 are pressed, the entered value will not be saved, and simply move the flashing highlight to the subsequent line. As will be understood, all numerical parameters may be set and modified as set forth above.

Referring back now to FIG. 4, upon confirming and/or entering of the various parameters, or after selecting a RESUME operation, the user is again presented with a menu for selecting between RUN, REVIEW, OPTIONS, or PRIME. Where the user selects PRIME 482 by pressing prime/bolus key 515, there is output a second screen with instructions on how to prime pump 10, specifically, by continuing to press prime/bolus key 515, pump 10 operates and cycles the medication therethrough to eliminate any air bubbles as in step 492. Where the user selects REVIEW 484, the operation returns to step 463, and the user may review, and if necessary, modify the parameters currently set. Where the OPTIONS 481 is selected by pressing options function key 502, further options relating to the operation of pump 10 may be modified. Once RUN 483 is selected by pressing run/pause function key 503, infusion 493 begins. With reference to FIG. 3, pump 10 has switched states from configuration state 301 to infusion state 302.

Figure 8A:
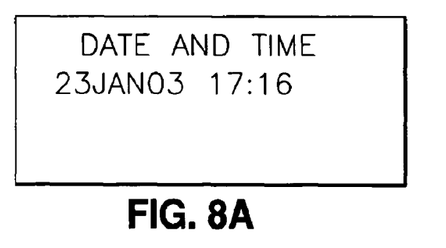
FIGS. 8a-8h are exemplary displays of informational screens when activated by function keys during the infusion state in accordance with an aspect of the present invention.
Figure 8B:
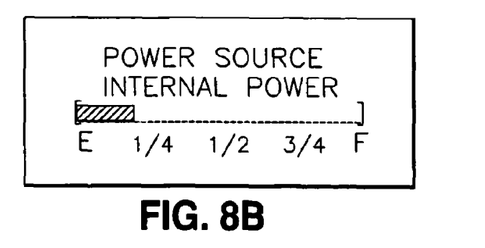
Figure 8C:
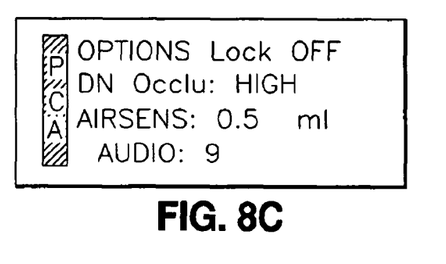

Referring to FIGS. 2, 3 and 5, it will be understood that generally, keypad 20 possesses different functionality in configuration state 301 than in infusion state 302. More particularly, during infusion state 302, first numerical function key 521 displays the date and time as shown in FIG. 8a. However, during configuration state 301, first numerical function key 521 is operative to signal a "1" input to monitor and control unit 130. Further, during infusion state 302, second numerical function key 522 displays the status of the power source and how much battery power is remaining in a graphical fashion as illustrated in FIG. 8b. Whereas in configuration state 301, second numerical function key 522 is operative to input a "1" to monitor and control unit 130. Still further, during infusion state 302, the third numerical function key 523 displays the global options as set in step 491 of FIG. 4, illustrated in FIG. 8c, but during configuration state 301, the key is operative to input a "3." Moreover, during infusion state 302, fourth numerical function key 524 is operative to "hold" a screen for a set period of time, preferably 6 seconds. It will be understood that various screens are displayed at Shorter intervals when this functionality is not activated.

Figure 8D:
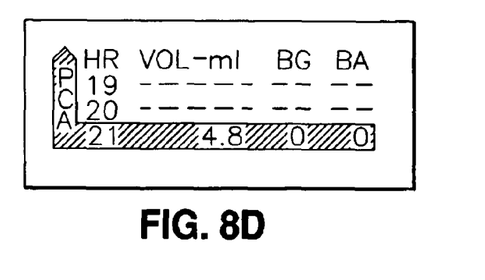

Additionally, during infusion state 301, fifth numerical function key 525 activates an hourly infusion log as illustrated in FIG. 8d. In this screen, up and down arrow keys 511 and 512 may be pressed to review the previous hours of treatment not displayed on display 22. As will be apparent, fifth numerical function key 525 is operable to input a "5" when in configuration state 301. By activating sixth numerical function key 526, the details of the treatment, that is, the parameters as set in one of steps 472 or 473 may be viewed, shown in FIG. 8e. However, unlike in configuration state 301, the parameters may not be modified. In configuration state 301, of course, sixth numerical function key 526 is operable to signal a "6" to monitor and control unit 130.

Figure 8E:
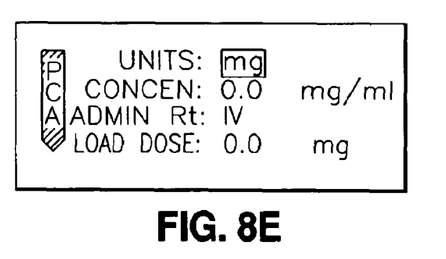
Figure 8F:
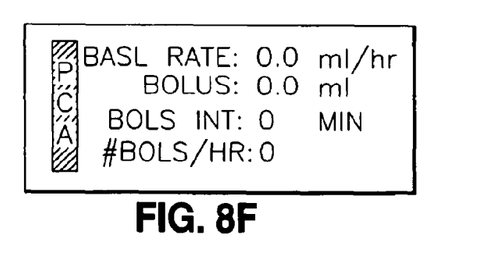
Figure 8G:
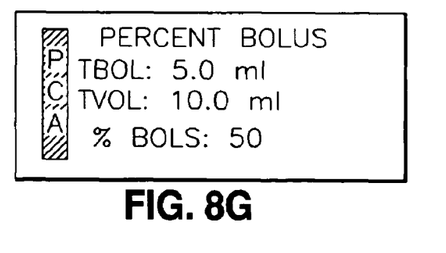

In infusion state 302, seventh and eighth numerical function keys 527 and 528 are operable to display bolus options and information. As described above, a bolus may be electrically connected to pump 10, transmitting a signal to monitor and control unit 130 through serial communications port 137 whenever it is activated by a user. Such activations are then store in memory module 130. As illustrated in FIG. 8f, activating seventh numerical function key 527 activates the bolus information screen, and as illustrated in FIG. 8e, activating eighth numerical function key 528 activates the bolus percentage screen. By now it will be readily apparent that seventh and eighth numerical function keys 527 and 528 are operable to signal a "7" and "8," respectively, to monitor and control unit 130 when pressed during the configuration state 301.

Figure 8H:
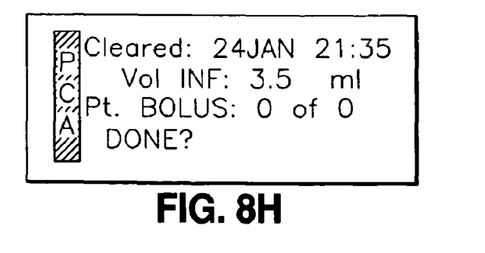

Ninth numerical function key 529 is operable to clear the treatment logs while in infusion state 302, and displays the results of the operation thereby as illustrated in FIG. 8h. While in configuration state 301, ninth numerical function key 529 is operable to transmit a "9" to monitor and control unit 130. It should be noted that tenth numerical function key 520 does not have a secondary function in infusion state 302, but is operable to transmit a "0" to monitor and control unit 130 during configuration state 301. It should be further noted that prime/bolus key 515 is operable to assist in priming pump 10 during configuration state 301, and in infusion state 302, it is operable to activate a bolus.

While reference has been made to a variety of different screens and corresponding key pressed which activate the same, the present invention is not limited to the particular information provided as illustrated in FIGS. 8a-8h. Any suitable, relevant information stored in memory module 134 or being processed in monitor and control unit 130 may be shown to display 22.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

What is claimed is:

1. An infusion pump having a configuration state during which configuration data is input to the pump for controlling a subsequent infusion operation and an infusion state during which the pump executes an infusion operation in accordance with inputted configuration data, the infusion pump comprising:
   a housing configured to receive a tube through which infusion fluid is pumped;
   a data processor contained within the housing;
   a display electrically connected to the data processor and affixed to the housing; and
   a plurality of function keys electrically connected to the data processor and affixed to the housing, each of the plurality of function keys corresponding to a respective numeric character, wherein at least one of the function keys is operable while the infusion pump is in the configuration state to input the numeric character to said data processor, and is operable while the infusion pump is in the infusion state to cause a predetermined information screen to be displayed by the display.

2. The infusion pump according to claim 1, wherein the plurality of function keys includes a function key operable while the infusion pump is in the infusion state to cause a displayed information screen to be held by the display for a predetermined period of time.

3. The infusion pump according to claim 1, further comprising a memory module electrically connected to the data processor, wherein the memory module stores configuration data and operational data.

4. The infusion pump according to claim 1, wherein the plurality of function keys includes a function key operable while the infusion pump is in the infusion state to clear data from the memory module.

5. The infusion pump according to claim 1, further comprising an additional function key operable while the infusion pump is in the configuration state to cause instructions for priming the pump to be displayed by the display, and is operable while the infusion pump is in the infusion state to send a bolus activation signal to an external bolus electrically connected to the data processor.

6. The infusion pump according to claim 1, wherein the predetermined information screen includes a current date and time.

7. The infusion pump according to claim 1, wherein the predetermined information screen includes electrical power source information.

8. The infusion pump according to claim 1, wherein the predetermined information screen includes currently set global options.

9. The infusion pump according to claim 1, wherein the predetermined information screen includes a log of infusion history.

10. The infusion pump according to claim 1, wherein the predetermined information screen includes currently set fluid medication infusion options.

11. The infusion pump according to claim 1, wherein the predetermined information screen includes a log of bolus activation history.

12. The infusion pump according to claim 1, wherein the plurality of function keys each have a unique predetermined information screen respectively associated therewith.

13. The infusion pump according to claim 1, wherein the tube is a fluid line.

14. The infusion pump according to claim 1, wherein the plurality of function keys are operable without depressing another key.

15. The infusion pump according to claim 1, wherein the plurality of function keys are repurposed during an infusion state.

16. The infusion pump according to claim 1, wherein the predetermined information screen corresponds to current operational information.

17. The infusion pump according to claim 1, wherein the predetermined information screen is displayed without depressing another function key.

\* \* \* \* \*